United States Patent [19]
Rosenberg

[11] Patent Number: 4,597,739
[45] Date of Patent: Jul. 1, 1986

[54] TOW ELEMENT BRACKET SYSTEM FOR TRUE STRAIGHT WIRE ORTHODONTICS

[76] Inventor: Farel Rosenberg, 10535 Wilshire Blvd. #1811, Los Angeles, Calif. 90024

[21] Appl. No.: 736,362

[22] Filed: May 21, 1985

[51] Int. Cl.[4] ............................................. A61C 3/00
[52] U.S. Cl. .......................................... 433/16; 433/9
[58] Field of Search ................... 433/16, 8, 9, 10, 13, 433/14, 15

[56] References Cited

U.S. PATENT DOCUMENTS

| | | | |
|---|---|---|---|
| 2,908,974 | 10/1959 | Stifter | 433/16 |
| 3,423,833 | 1/1969 | Pearlman | 433/16 |
| 3,660,900 | 5/1972 | Andrews | 433/16 |
| 3,721,005 | 3/1973 | Cohen | 433/16 |
| 3,922,787 | 12/1975 | Fischer et al. | 433/15 |
| 4,139,945 | 2/1979 | Di Giulio | 433/16 |
| 4,249,897 | 2/1981 | Anderson | 433/16 |

OTHER PUBLICATIONS

"IPB" Ad, Guild Arts + Crafts, Inc., 10-20-66.

Primary Examiner—John J. Wilson
Attorney, Agent, or Firm—Gilbert Kivenson

[57] ABSTRACT

The present invention relates to a two piece, adjustable, orthodontic bracket system to which a flexible archwire is tied. The distortions at various points along the archwire are automatically set by specially-oriented archwire slots cut into the face of interchangeable working brackets. Maintenance or modifying of any desired tooth position during treatment is done through the use of these working brackets which are inserted and removed from their bracket support bases as case needs dictate. The dentist or orthodontist, as a result need not make bends in the wire or change bracket positions on the teeth as in prior art.

From the amount and direction of the local distortion at each bracket, tooth moving forces are derived which are of the correct magnitude and direction to achieve in time the proper orientation of the teeth.

5 Claims, 41 Drawing Figures

|                                                      | (I)     | (II)    | (III)   | (IV)    |
|------------------------------------------------------|---------|---------|---------|---------|
| Up-down                                              | down    | up      | up      | down    |
| In-out                                               | neutral | neutral | neutral | neutral |
| Torque                                               | neutral | neutral | neutral | neutral |
| Rotation (perpendicular to plane of paper)           | ccw     | cw      | cw      | ccw     |
| Angulation (parallel to plane of paper)              | cw      | ccw     | cw      | ccw     |
| Working slot                                         | 20      | 19      | 20      | 19      |

TOW ELEMENT BRACKET SYSTEM FOR TRUE STRAIGHT WIRE ORTHODONTICS

INTRODUCTION

In orthodontic practice archwire bending is a time-consuming but essential component of the treatment procedure. Tooth alignment problems are corrected by applying appropriate bends to a generally U-shaped archwire. When out-of-line teeth are tied to this wire by means of orthdontic brackets whose wire-receiving slots are used as attachment areas, forces result which move these teeth into a desired orientation over a period of time. Teeth having proper alignment initially are tied to unbent portions of the wire and may serve to define an "ideal" orientation to which the other teeth are directed.

The modes of tooth movement required for misalignment correction are: up-down (tooth extrusion or intrusion); in-out (movement towards the tongue or cheek side of the mouth); rotation (turning of the tooth, in its socket-clockwise or counterclockwise when viewed from above-without other movement); angulation (tilting of the tooth towards the front or back of the dental arch); torque (twisting of the tooth towards the tongue or cheek side of the mouth).

Present day orthodontic brackets are applied to the teeth by bonding. Each bracket is provided with a slot for archwire containment and ligature tie grooves to receive elastic rings or tie wires for securing the archwire to each bracket. (In an older technique the brackets were first welded to metal bands; the latter were slipped over the teeth and cemented into place.) One-piece orthodontic brackets are cast or molded to have a fixed, "average" amount of torque, in-out, angulation and sometimes rotation built into the bracket base. This is done to limit wire bending somewhat for average, normally-shaped teeth and assumes that the bracket will be placed and bonded in a precisely determined position on the tooth. Since provision has only been made for "average" teeth in these fixed, one piece systems, there is no allowance for normally-occurring differences in tooth anatomy or in bracket placement errors. Wire bending is therefore required to correct the alignment problem. A way of eliminating wire bending is by iterated rebonding of the brackets for a better position on their respective teeth, but this is a time consuming process.

Some previous attempts have been made to design a two-piece bracket system (i.e. a bracket and a holder). The method proposed by Stifter (U.S. Pat. No. 2,908,974) does eliminate some wire bending but requires the orthodontist to stock a very large number of specially slotted brackets. Aside from the initial expense, the identification of the proper unit for each tooth would be time consuming. In the prior art it has also been necessary to remove the bracket from its holder in a mesial-distal (side-to-side) movement, a difficult operation particularly with small, closely-positioned teeth. This side-to-side movement may result in unwanted bracket interferences when the orthodontist needs to replace them. In addition, Stifter's apparatus does not permit the maintenance of favorable force vectors on a given tooth while simultaneously altering other force vectors to achieve a desired alteration in tooth position.

OBJECTIVES

It is an objective of the present invention to provide a bracket support base to which a working bracket can easily be attached or detached. The bracket support base will hold the working bracket firmly but will release it readily when required.

It is a second objective of the invention to provide a series of slot-bearing working brackets which contain one or more slots so that multiple functions can be obtained with each working bracket. In this way the number of working brackets required can be drastically reduced.

It is a third objective of the invention to provide means for inserting each working bracket and then securing it in its bracket support base in flush, congruent and specific positions. A chosen bracket will then provide the type and intensity of tooth movement desired and will present smooth, continuous external surfaces in the mouth and thus promote cleanliness. Tooth movement will be determined by slot positions cut in the face of the working bracket.

It is a fourth objective of the invention to standardize the system so that all the working brackets are universal and fit any support bracket.

It is a fifth objective of the invention to provide a system which also operates in lingual orthodontics (the brackets and wire are on the tongue side of the teeth so as to decrease frontal visibility).

It is a sixth objective of the invention to provide means to accomplish tooth rotation automatically by means of a slot in the working bracket having a depth which varies linearly in a horizontal direction.

It is a seventh objective to provide means for applying all of the modes of tooth movement—up-down, in-out, rotation, torque and angulation—simultaneously and in varying amounts as required.

These and other objectives will be explained by reference to the accompanying drawings.

DESCRIPTION OF THE INVENTION

Figure 1:
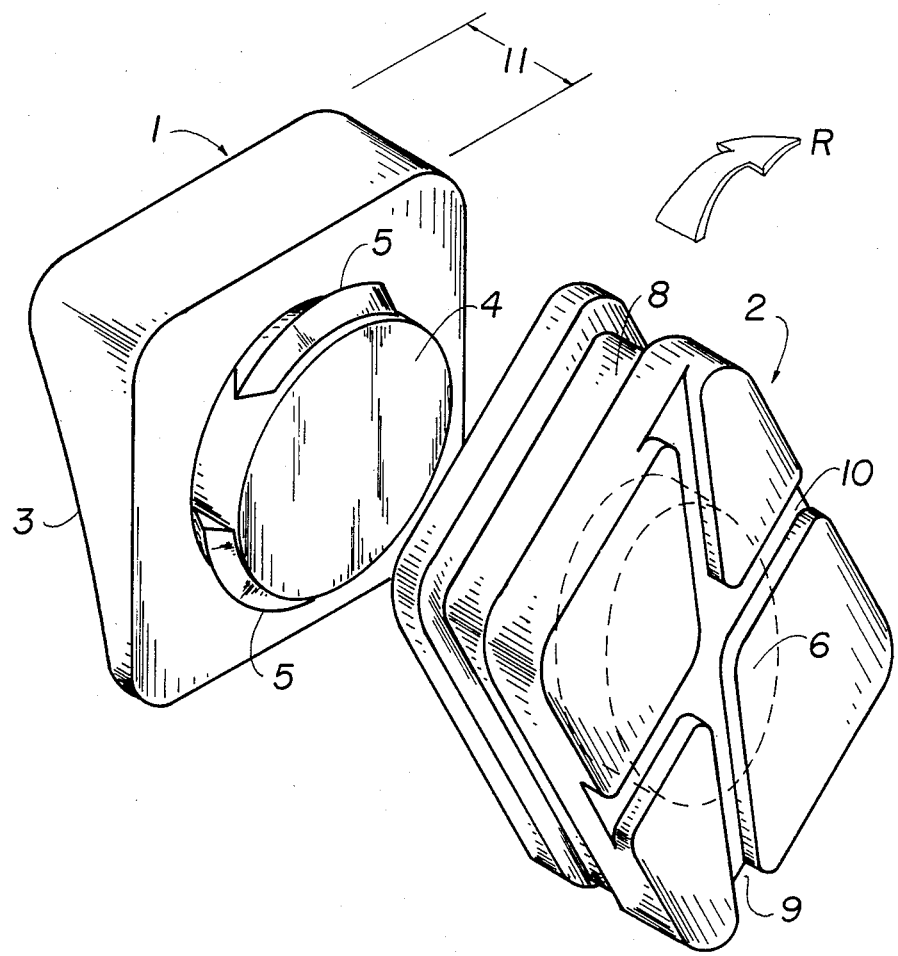
FIG. 1 is a perspective view of the two components of the invention: the bracket support base and the working bracket.

FIG. 1 shows both components of the invention in an isometric view. The bracket support base 1 is contoured at 3 to conform to the shape of the individual tooth to which it is bonded. The varying dimension 11 is specific for each tooth to equalize its varying individual thickness and contour and is chosen to permit the use of a straight archwire (i.e. conforming to the dental arch without initial indentation) as is presently known to the art. An integral part of the bracket support base is the coupling cylinder 4 which is provided with a four male locking wedges 5 equally spaced about its periphery.

Figure 2:
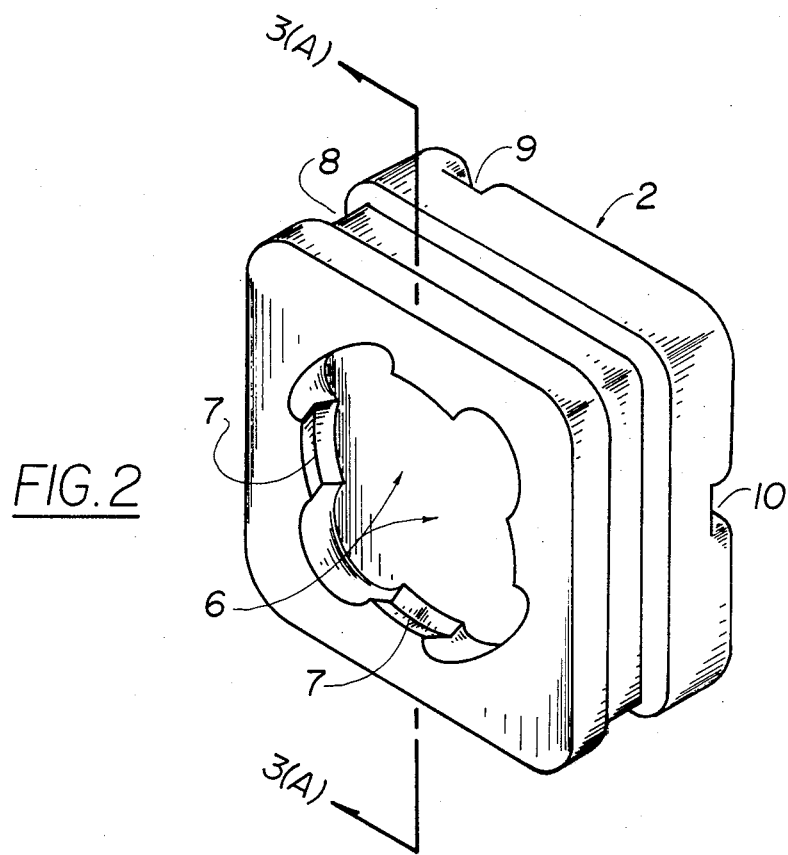
FIG. 2 is an isometric view of the rear side of the working bracket.
Figure 3A:
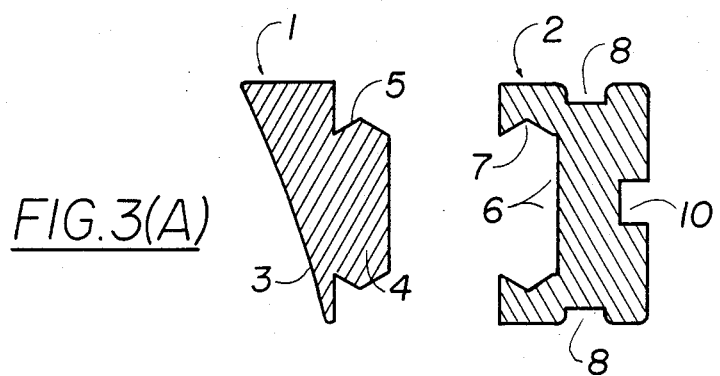
FIG. 3(A) is a cross section of the bracket support base and the working bracket prior to coupling.
Figure 3B:
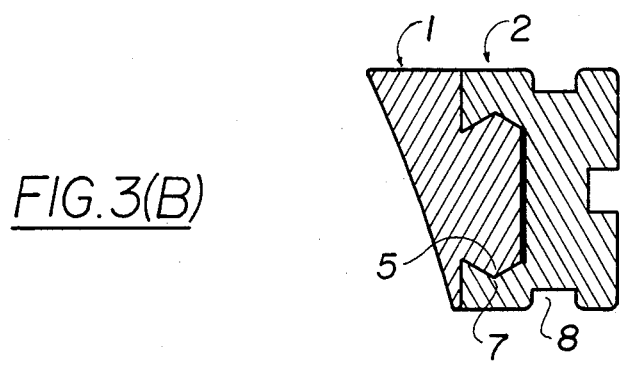
FIG. 3(B) shows the two pieces as coupled indicating the flush and congruent nature of the junction.

The working bracket assembly 2 (FIGS. 2, 3(A) and 3(B)) contains the cylindrical opening 6, the female receptor grooves 7 and archwire slots such as 9 and 10 in its face. To join the working bracket to the bracket support base (FIGS. 3(A) and 3(B)), the coupling cylinder 4 of the bracket support base is first inserted into the cylindrical opening 5 in an orientation which permits the four male locking wedges 5 to pass between the four female receptor grooves 7. There will be four positions of the working bracket in which this is possible. After this, turning of the working bracket in the direction R (FIG. 1) through 45 degress will engage the four male wedges 5 with the four female receptor grooves 7 and lock the working bracket to the support bracket base in one of four specific positions. FIG. 3(A) shows in cross section the relation between the male locking wedges and the female receptor grooves when the working bracket and bracket support base are in line. FIG. 3(B) indicates in cross section the working bracket locked to the bracket support base.

From the above description it will be apparent that the locking positions are separated by 90 degrees. If two archwire slots are cut into a face of a working bracket block, they can function as four slots when the above-described insertion mechanism is applied. It is only necessary to attach a suitable working bracket and place it in the proper orientation with respect to its bracket support base to achieve any desired mode or combination of modes of tooth movement. The ligation tie grooves 8 are used for securing the archwire into the working horizontal slot in the working bracket using tie wires or elastic rings.

Figure 4:
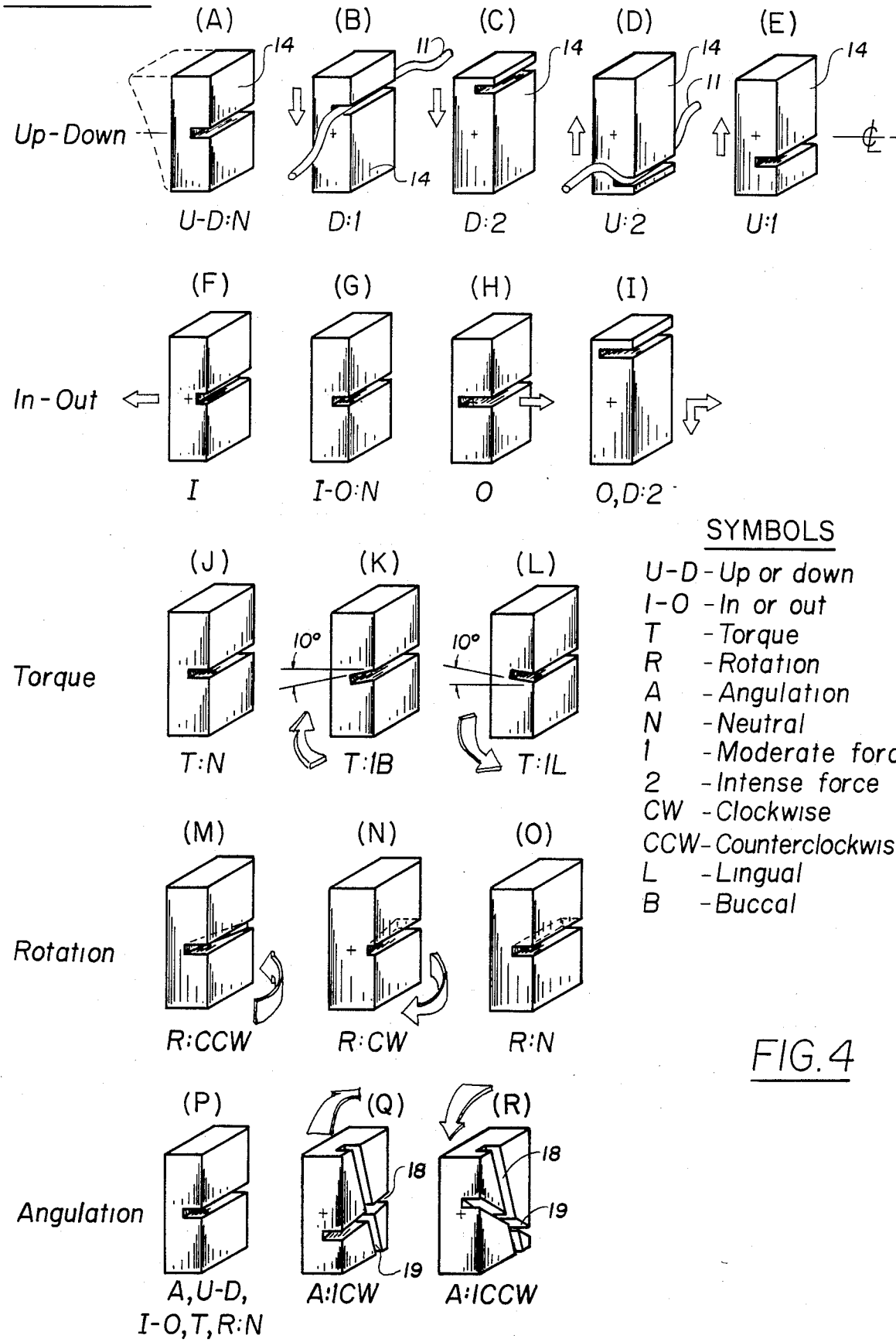
FIG. 4 is a table of isometric views of a simplified, one-slot working bracket indicating how individual slots would be orientated to achieve various degrees of up-down, in-out, torque, rotation and angulation modes of tooth movement.

FIG. 4 shows how a single archwire slot will provide the various forces required for orthodontic correction. The effects of the various slots shown in FIG. 4 are described in terms of their use in the lower left, cheekside quadrant of the mouth. Many, but not all, of the working brackets will produce reverse forces when used in other quadrants or in lingual orthodontics. The in-out slots of FIGS. 4(F) and 4(H) will generate forces in the same direction in all four quadrants and when used on either the tongue or cheek side of the mouth. FIG. 4(B) illustrates the up-down working mode of the system. Here the slot is above center (the face of the working bracket is at 14). In order for archwire 11 to pass through the slot it must be locally distorted in an up direction. The elasticity of the wire now exerts a downward force on the bracket and the tooth to which it is attached. Stress relief is not possible except through tooth intrusion over a period of time. A stronger instrusion force creating more tooth movement is obtained with the working bracket shown in FIG. 4(C) because the higher slot position requires more local distortion of the archwise. If the working bracket of FIG. 4(C) is now rotated through 180 degrees and rejoined to the bracket support base as shown in FIG. 4(D), an upward or extrusion force is produced when the archwire is attached. A milder extrusion force with lesser tooth movement would be obtained by rotating through 180 degrees the working bracket of FIG. 4(B) (whose slot is not as far removed from center). This is shown in FIG. 4(E). If no vertical force is required, the neutral working bracket of FIG. 4(A) would be employed. The neutral working bracket serves to create a reference plane from which the archwire can be flexed in any direction to fit the slots of working brackets on adjacent teeth.

In and out forces, as mentioned above, would be created by shallow or deep slots respectively as shown in FIGS. 4(F) and 4(H) which deviate from a "neutral" depth shown in FIG. 4(G). In FIG. (I) is a bracket having a deep slot which is also above center. In this orientation the bracket and archwire would exert both outward and downward forces. Rotation of 180 degrees would bring about outward and upward forces.

Torque is brought about by inclination of the rectangular archwire slot and the use of a close-fitting rectangular archwire. This produces a torque effect, moving the tooth either in a buccally-directed or lingually-directed twisting motion, the direction depending on the working bracket slot orientation, FIGS. 4(K) and 4(L).

Rotation is accomplished by sloping the bottom of the slot as shown in FIG. 4(M). The rotational direction is reversed by turning the bracket through 180 degrees (FIG. 4(N). If desired, the rotation force intensity can be varied by providing brackets with differing bottom slopes. It will also be noted that moving the slot toward the top or bottom of center will produce up-down as well as rotational forces. "Neutral rotation" is shown in FIG. 4(O).

For angulation (the tilting of the tooth in a mesial or distal direction) obliquely cut slots are used. In FIG. 4(Q) the slot shown in the horizontal orientation will produce clockwise tilting of medium intensity. When rotated through 90 degrees as shown in FIG. 4(R) the now-horizontal slot 19 will give clockwise tilting of the tooth.

Figure 5:
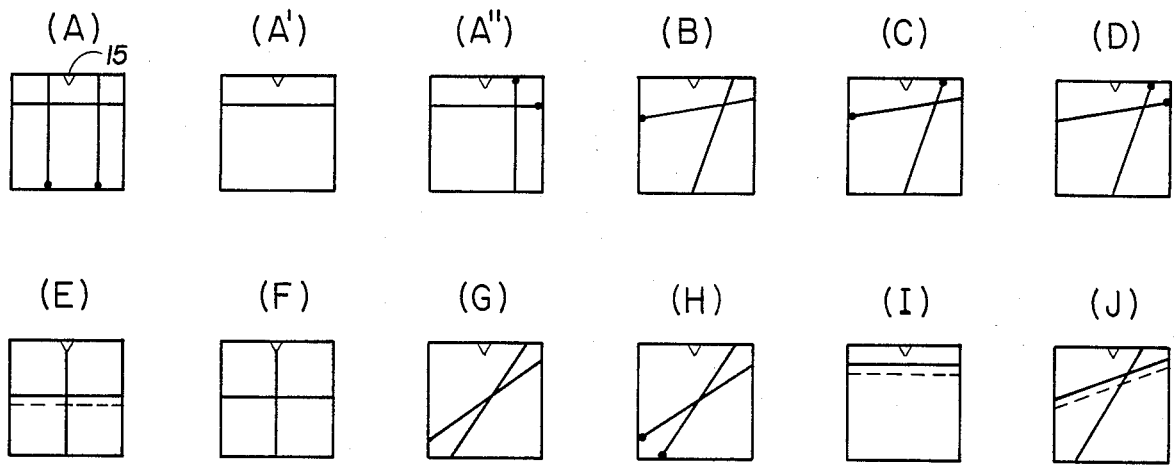
FIG. 5 is a symbolic table illustrating various cross-cut, vertical and horizontal slot combinations and how various orientations of the working bracket will achieve desired tooth movements.

A major feature of the invention is illustrated in FIG. 5. with the exception of FIGS. 5(A) and 5(A') all the brackets contain two crosscut slots. Slots of uniform depth are designated by straight lines in FIG. 5. Slots of non-uniform depth are market with a dot at the deepest end. A dotted line beneath or above a solid indicates a torque-producing slot the bottom of which is either above or below the face (as previously shown in FIGS. 4(K) and 4(L). The mark 15 identifies the top of the bracket and the starting position from which all turns are made. The vertical or nearly vertical slot in each position is inactive; the archwire occupies the "working" horizontal or nearly horizontal slot. The bracket shown in FIG. 5(A) utilizes three slots because it is possible with this configuration to obtain a maximum number of functions without interference between slots. In the top position of the bracket a downward force would be obtained. Turning the working bracket by 90 degrees to the right will permit the two "new" horizontal slots to rotate the tooth in a counterclockwise direction with an accompanying downward force of high intensity (using the upper slot) or with an upward force of high intensity (using the lower slot). This arrangement could be replaced by the two pieces shown in FIGS. 5(A') and 5(A") if the number of slots per bracket was to be limited to two or less. The slot arrangements shown in FIGS. 5(B), (C), (D), (E), (F), (G), (H), (I) and (J) allow a very large number of force vectors to be generated both by choice of working bracket and its desired position in the bracket support base. The cross-cut combinations shown in FIG. 5 and similar combinations make up a preferred embodiment of the invention in which less than 100 separate working bracket pieces constitute a complete system which give over 400 ready-made combinations of tooth moving forces per tooth before any archwire bending or bracket rebonding might be required as compared to a maximum of 3 or 4 positions in prior art.

Figure 6:
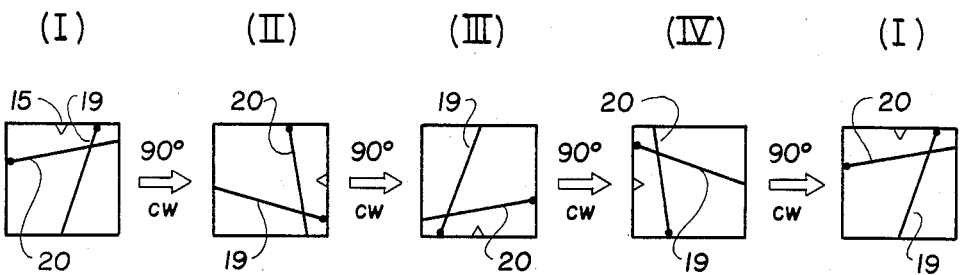
FIG. 6 shows the effects of moving one of the working brackets of FIG. 5 through its four possible positions in a bracket support base.

FIG. 6 illustrates the four positions into which the working bracket of FIG. 5(D), containing the slots 19 and 20, can be locked. In position I a down force, counterclockwise rotation and clockwise angulation forces will be simultaneously exerted on the particular tooth to which it is attached. The in-out and torque forces will in this case be neutral. Turning of the working bracket through 90 degrees and locking in each of the other positions will alter these forces as shown in the accompanying table in FIG. 6.

Each bracket can be color and symbol coded so that selction from a subdivided tray containing the various types is readily made. The various favorable force vectors can be accurately reproduced from tooth to tooth. Each working bracket is designed to fit any bracket support base. This universality permits any and all working brackets to be used with any tooth. Continuing treatment can be accomplished easily be removing and replacing successive working brackets in their bracket support bases as necessary. All five tooth movement force vectors—i.e. up-down, in-out, torque, angulation and rotation—can be simultaneously applied through the proper choice of working bracket to achieve the desired tooth movement.

Figure 7:
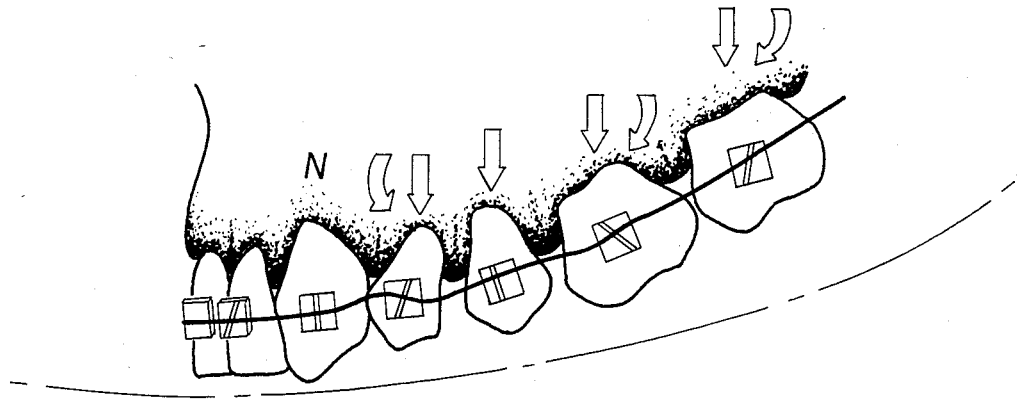
FIG. 7 indicates the use of the invention at the start of the process of moving teeth into proper alignment.
Figure 8:
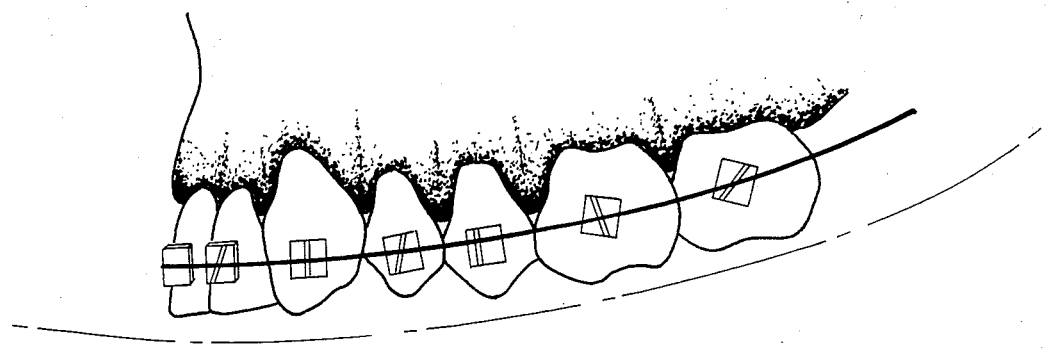
FIG. 8 illustrates the condition of FIG. 7 corrected.

FIG. 7 shows how the two piece system would appear as applied to misaligned teeth. In FIG. 8 the forces produced by the archwire have taken effect; the teeth are now in a normal orientation.

The invention will be especially useful in the more recent system of lingual orthodontics because the present practice of wire bending and bracket re-cementing is particularly difficult on the tongue side of the teeth.

Other embodiments of the present invention can be readily conceived. A circular form of working bracket can for example be used to eliminate sharp edges in the mouth. Other types of ligature arrangements can be added.

I claim:

1. A two piece adjustable bracket system for straight wire orthodontic treatment comprised of:
   (a) a series of bracket support bases individually contoured on one side to permit bonding to each tooth, each bracket support base being of a thickness to establish, with its tooth, a vertical faces which together with the corresponding vertical faces of other bonded bracket support bases creates a symmetrical archform which compensates for the width and contour variations of the teeth to which they are bonded;
   (b) a series of rectangular working brackets each containing a plurality of archwire slots;
   (c) a coupling means integral with each bracket support base and with each working bracket rigidly, but detachably, joins a support base to a bracket in a flush fit and having means for attaching said bracket to said support base in any of four angular positions;
   whereby the following improved treatment procedure may be carried out:
   a bracket support base having a tooth side contour conforming in both horizontal and vertical direction, and of proper width and height is bonded to each tooth;
   a working bracket having archwire hodling means particularly suited for the type of orthodontic movement required of that tooth is coupled to the corresponding bracket support base in any chosen one of four possible positions by use of the said coupling means;
   a flexible archwire is positioned in and held to a desired working bracket to produce simultaneously the desired in-out, up-down, rotation, torque and angulation tooth movements needed to bring all the teeth into the alignment required without the need for archwire bending and rebonding of the bracket support base, while allowing subsequent changes in any of the said tooth movements to be rapidly and conveniently made.

2. A two piece bracket system as described in claim 1 in which said slots are cross-cut into the face of the working bracket, each slot being capable of locally distorting an archwire, when the archwire is introduced into the slot and held, over a period of time, the overall effect being to produce in-out, up-down, rotation, torque and angulation forces.

3. A two piece bracket system as described in claim 1 in which said archwire holding means is comprised of a peripheral groove in the edge of the working bracket, posterior to the slots, to receive ligation tie-in means so that an archwire passing through any distortion-producing slot can be tied to the working bracket.

4. A two piece bracket system as described in claim 1 in which said coupling means between the bracket support base and the working bracket is comprised of:
   (a) a cylindrical member extending from the bracket support base and provided along its periphery with four tapering, triangularly shaped male locking wedges;
   (b) a corresponding, cylindrically-hollowed portion in the working bracket which contains four traiangularly-grooved, female segments to receive said male locking wedges; whereby placing of the working bracket so that the cylindrical member of the bracket support base enters the said cylindrically-hollowed portion and then turning the working bracket through 45 degrees locks the two pieces together in one of four possible positions each separated by 90 degrees, the coupling so achieved providing a flush, congruent and smooth junction which minimizes food trapping, is non-irritating and hygienic.

5. A two piece bracket system as described in claim 4 in which said coupling means is sized to permit the locking of any working bracket to any bracket support base whereby complete interchangeability of the working brackets is obtained.

* * * * *